US010507205B2

(12) United States Patent
Hermann

(10) Patent No.: US 10,507,205 B2
(45) Date of Patent: Dec. 17, 2019

(54) METHODS OF TREATING OPIATE DEPENDENCY AND PREVENTING NON-ORAL OPIATE ABUSE AMONG OPIATE ADDICTS

(71) Applicant: PURDUE PHARMACEUTICAL PRODUCTS L.P., Stamford, CT (US)

(72) Inventor: Lars Hermann, Schindellegi (CH)

(73) Assignee: Purdue Pharmaceutical Products L.P., Stamford, CT (US)

( * ) Notice: Subject to any disclaimer, the term of this patent is extended or adjusted under 35 U.S.C. 154(b) by 0 days.

(21) Appl. No.: 15/187,374

(22) Filed: Jun. 20, 2016

(65) Prior Publication Data

US 2017/0136005 A1 May 18, 2017

Related U.S. Application Data

(63) Continuation of application No. 12/161,397, filed as application No. PCT/EP2007/050540 on Jan. 19, 2007, now abandoned.

(30) Foreign Application Priority Data

Jan. 19, 2006 (EP) .................................... 06100578

(51) Int. Cl.
| | |
|---|---|
| A61K 31/485 | (2006.01) |
| A61K 9/00 | (2006.01) |
| A61K 9/20 | (2006.01) |
| A61K 9/48 | (2006.01) |
| A61K 45/06 | (2006.01) |

(52) U.S. Cl.
CPC .......... *A61K 31/485* (2013.01); *A61K 9/0053* (2013.01); *A61K 9/2027* (2013.01); *A61K 9/4808* (2013.01); *A61K 9/4825* (2013.01); *A61K 9/4866* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,769,372 A | 9/1988 | Kreek | |
| 5,580,876 A | 12/1996 | Crain et al. | |
| 5,672,360 A * | 9/1997 | Sackler | A61K 9/2081 424/468 |
| 6,228,863 B1 * | 5/2001 | Palermo | A61K 31/44 514/282 |
| 2004/0110781 A1 | 6/2004 | Harmon et al. | |
| 2004/0131552 A1 | 7/2004 | Boehm | |
| 2005/0063909 A1 | 3/2005 | Wright, IV et al. | |
| 2005/0181046 A1 | 8/2005 | Oshlack et al. | |
| 2005/0191244 A1 | 9/2005 | Bartholomaus et al. | |
| 2007/0264326 A1 | 11/2007 | Guimberteau et al. | |

FOREIGN PATENT DOCUMENTS

| | | |
|---|---|---|
| DE | 4325465 A1 | 2/1995 |
| EP | 0682945 A2 | 11/1995 |
| EP | 0914823 A1 | 5/1999 |
| EP | 1348429 A2 | 10/2003 |
| EP | 1604666 A1 | 12/2005 |
| GB | 1390772 A | 4/1975 |
| GB | 2438401 A | 11/2007 |
| WO | WO-9422431 A1 | 10/1994 |
| WO | WO-9733566 A2 | 9/1997 |
| WO | WO-9932119 A1 | 7/1999 |
| WO | WO-9940898 A2 | 8/1999 |
| WO | WO-0158447 A1 | 8/2001 |
| WO | WO-0158451 A1 | 8/2001 |
| WO | WO-02092060 A1 | 11/2002 |
| WO | WO-03084504 A2 | 10/2003 |
| WO | WO-2004026283 A1 | 4/2004 |
| WO | WO-2004108109 A1 | 12/2004 |
| WO | WO-2006079550 A2 | 8/2006 |
| WO | WO-2007149438 A2 | 12/2007 |

OTHER PUBLICATIONS

Kraigher et al. in Eur Addict Res 11:145-151 (2005).*
Loimer et al. in Journal of Substance Abuse Treatment 8, 157-160 (1991).*
Ripamonti et al. in Journal of Clinical Oncology 16:3216-3221 (1998).*
Reliatard Investigatorr's Brochure Reliatard 200 mg Retard-Granulat Modified-release granules (2009) (Year: 2009).*
Mitchell, T.B., et al., "Comparative pharmacodynamics and pharmacokinetics of methadone and slow-release oral morphine for maintenance treatment of opioid dependence," *Drug and Alcohol Dependence* 72:85-94, Elsevier Ireland, Inc., Ireland (2003).
Loimer, N., et al., "Combined Naloxone/Methadone Preparations," *Journal of Substance Abuse Treatment* 8:157-160, Pergamon Press, United States (1991).
Kraigher, D., et al., "Use of Slow-Release Oral Morphine for the Treatment of Opioid Dependence," *Eur Addict Res* 11:145-151, Karger AG, Basel, Switzerland (2005).
Hagers Handbuch der Pharmazeutischen Praxis 5, Received at the EPO on Feb. 24, 2011, 7 pages (1995).
"Table A-II-1, Pharmacokinetic Data" in *Goodman & Gilman's The Pharmacological Basis of Therapeutics Tenth Edition*, p. 1986, The McGraw-Hill Companies, Inc., United States (2001).
SmPC for Substitol "Substitol retard 120 mg—Kapseln" 4 pages.
SmPC for Valoron "Valoron® N retard" 20 pages, Jan. 1998.
Klinische Pharmakologie "Wörterbuch der Klinischen Pharmakologie," Received at the EPO on Sep. 5, 2011, 4 pages (1980).
SmPC for Andolor drops "Gebrauchsinformation: Information für den Anwender Andolor® Tropfen," 6 pages.

(Continued)

*Primary Examiner* — Dennis Heyer
(74) *Attorney, Agent, or Firm* — Sterne, Kessler, Goldstein & Fox P.L.L.C.

(57) ABSTRACT

The present invention relates to the use of an inseparable combination of morphine and at least one opiate antagonist with a bioavailability of less than 5% on oral administration for producing a medicament to be administered orally for treatment of opiate dependency in humans and to the use of an inseparable combination of an opiate and at least one opiate antagonists with a bioavailability of less than 5% on oral administration for producing a medicament to be administered orally for prevention of non-oral opiate abuse in opiate addicts.

6 Claims, No Drawings

(56) References Cited

OTHER PUBLICATIONS

SmPC for Tilidin Hexal Capsules "Gerbrauchsinformation: Information für den Anwender Tilidin HEXAL® comp Kapseln," 2 pages.
SmPC for Tinalox "Gerbrauchsinformation: Information für den Anwender Tinalox, Tropfen zum Einnehmen, Lösung," 5 pages.
SmPC for Valoron N "Gerbrauchsinformation: Information für den Anwender Valoron® N Tropfen zum Einnehmen, Lösung," 7 pages.
SmPC for Valoron "Valoron®," 6 pages.
Giacomuzzi, S.M., et al., "Substitutionsbehandlung und Lebensqalität: Methadon vs. retardiertes Morphinsulfat-eine Vergleichsstudie," (2001) (English language abstract on first page).
Callahan, R.J., et al., "Functional Inhibition by Methadone of N-Methyl-D-Aspartate Receptors Expressed in *Xenopus* Oocytes: Stereospecific and Subunit Effects," *Anesth Analg* 98:653-659, International Anesthesia Research Society, United States (2004).
Gutstein, H.B., and Trujillo, K.A., "MK-801 inhibits the development of morphine tolerance at spinal sites," *Brain Research 626*:332-334, Elsevier Science Publishers B.V., Netherlands (1993).
Bell, J., et al., "The Acceptability, Safety, and Tolerability of Methadone/Naloxone in a 50:1 Ratio," *Experimental and Clinical Psychopharmacology 17(3)*:146-153, American Psychological Association, United States (2009).
German language Interlocutory Decision in the Opposition Proceedings for Application No. 07 704 010.3, dated Jul. 18, 2013, 21 pages.
"Investigator's Brochure Reliatard 200 mg Retard-Granulat Modified-release granules," Sponsored by Avelion GmbH, May 12, 2009, 2 pages.
English language translation of the Interlocutory Decision in the Opposition Proceedings for Application No. 07 704 010.3, dated Jul. 18, 2013, 21 pages.
"Proof of Principle Studies for a combination medication of naloxone and morphine Study 1," Nov. 19, 2007, 1 page.
"Study 2," Nov. 19, 2007, 1 page.
Unverified English language translation of "Package information leaflet for Valoron® drops for oral use, solution" 7 pages.
Unverified English language translation of "Valoron®" 5 pages.
English language translation for Hagers Handbuch der Pharmazeutischen Praxis 5, Received at the EPO on Feb. 24, 2011, 7 pages (1995).
English language translation for SmPC for Substitol "Substitol retard 120 mg—Kapseln" 17 pages.
English language translation for SmPC for Valoron "Valoron® N retard" 74 pages, Jan. 1998.
English language translation for Klinische Pharmakologie "Wörterbuch der Klinischen Pharmakologie," Received at the EPO on Sep. 5, 2011, 5 pages (1980).
English language translation for SmPC for Andolor drops "Gerbrauchsinformation: Information für den Anwender Andolor® Tropfen," 6 pages.
English language translation for SmPC for Tilidin Hexal Capsules "Gerbrauchsinformation: Information für den Anwender Tilidin HEXAL® comp Kapseln," 6 pages.
English language translation for SmPC for Tinalox "Gerbrauchsinformation: Information für den Anwender Tinalox, Tropfen zum Einnehmen, Lösung," 5 pages.
Crain, S.M., et al., "Ultra-low Concentrations of Naloxone Selectively Antagonize Excitatory Effects of Morphine on Sensory Neurons, thereby Increasing Its Antinociceptive Potency and Attenuating Tolerance/dependence During Chronic Cotreatment," Proceedings of the National Academy of Sciences of the United States of America 92(23):10540-10544, National Academy of Sciences, United States, (1995).
Heiden N.A., et al., "Effect of Intravenous Magnesium Sulphate in Reducing Irritability and Restlessness in Pure and Polysubstance Opiate Detoxification," Psychiatry Research, 135(1):53-63, Elsevier/North-Holland Biomedical Press, (May 2005).
Kreek M.J., et al., "Pharmacotherapy of Addictions," Nature Reviews Drug Discovery, 1(9):710-726, London, UK : Nature Pub. Group, (Sep. 2002).
Linzmayer L., et al., "[Electrodermal Activity in Heroin Addicts and Patients with Methadone and Morphine Substitution]," Wiener Medizinische Wochenschrift , 153(3-4):76-79, Wien : Springer Verlag, (2003).
Mendelson, J., et al., "Buprenorphine and Naloxone Interactions in Opiate Dependent Volunteers," Clinical Pharmacology and Therapeutics 60(1):105-114, Wiley, United States (1996).
Hu, Jialu, et al., "Internal Medicine," Higher Education Press, 1$^{st}$ edition, pp. 1249-1251 (2001).

* cited by examiner

METHODS OF TREATING OPIATE DEPENDENCY AND PREVENTING NON-ORAL OPIATE ABUSE AMONG OPIATE ADDICTS

The present invention relates to the use of a combination of morphine and at least one opiate antagonist, in particular naloxone, to treat opiate dependency in humans. The invention further relates to the use of a combination of an opiate and at least one opiate antagonist to prevent non-oral opiate abuse among opiate addicts.

Drug addiction continues to be a problem in our society. It is common knowledge that taking certain substances such as for example heroin leads to dependency. A distinction is made here between a physical dependency and mental drug dependency (drug addiction). Physical drug dependency occurs when there is an abrupt cessation or significant reduction in the quantity of the substance taken. There are withdrawal symptoms such as vomiting and cramps of the gastrointestinal tract. A distinction is made between this and actual drug addiction, mental dependency, which is regarded as a separate neurological disorder. Symptoms of drug addiction are a failure to control one's own use of the drug, self-endangerment and a compulsive desire to acquire the drug.

By drug addiction within the scope of the present invention is meant in particular an opiate dependency (mental and behavioural disorders due to opioids; F11 of ICD-10). A heroin dependency or opiate dependency can be treated particularly well with the present method.

Drug addiction is currently treated by switching the patient from a dangerous drug to a less dangerous substitute, or reducing the patient's dose under controlled conditions. However, for various reasons not every drug is accepted by patients. Methadone, heroin, buprenorphine and morphine are used as substitutes. Methadone is a synthetic opiate with the formula:

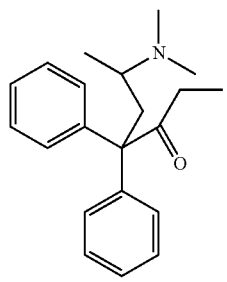 [SMILES: CCC(=O)C(CC(C)N(C)C)(c1ccccc1)c1ccccc1]

Methadone has been used as a substitute since the 1960s, both in the optically active L-form and in the racemate form. Methadone is suitable for satisfactorily alleviating withdrawal symptoms, especially in heroin patients. It has a longer-lasting effect than heroin, can be taken orally without any appreciable loss of effect and does not produce a "kick" (i.e. the especially euphoric feeling which is triggered e.g. by heroin and leads to drug addiction). In order to prevent an improper intravenous administration, methadone is often given in the form of a syrup mixed with sugar or orange juice in addiction treatment programmes.

However, the effect of methadone differs from one individual to another and its administration is therefore not simple. Methadone also produces a high level of dependency. Methadone withdrawal symptoms actually last longer than those of heroin. Methadone, like all opiates, leads to constipation, as it has a paralyzing effect on the gastrointestinal musculature. In addition, methadone seems to have significant side-effects.

A dosage form with retarded morphine and retarded naloxone is known from WO 97/33566 A2. This dosage form contains a semipermeable wall which surrounds a two-layered core consisting of an opioid (outer layer) and—separate from it—an antagonist (inner layer). The physical separation of the opioid and the antagonist means it is easy for the drug addict to obtain the opioid through separation measures, for example by first scraping off the outer wall of the dosage form and then removing the outer shell from the exposed core.

Controlled-release preparations based on retarded morphine and a retarded antagonist are known from WO 01/58447 A1. However, there is no indication that the antagonist is to have a low bioavailability.

Pain-therapy preparations based on retarded morphine and non-retarded naloxone are known from WO 99/32119 A1 and DE 43 25 465 A1, without affecting the field of application of the present invention.

Combination preparations consisting of particular opioid analgesics and naloxone are also known from the state of the art. The commercial product Talwin®Nx contains pentazocine and naloxone. The product Valoron®N contains tilidine and naloxone. However, these are painkillers to which the naloxone is added to prevent improper use as a drug. Thus far consideration has not been given to the use of these commercial products as drug substitutes. The emphasis in the state of the art has been more on attempts to make it impossible to use the corresponding preparations as drugs.

Furthermore, a combination of buprenorphine and naloxone is already known as a drug substitute. Because of the weak intrinsic activity of the substance, buprenorphine is suitable as a substitute for only some opiate addicts.

A need therefore exists for a different and improved drug-addiction treatment.

According to the present invention it was surprisingly found that a combination of morphine and at least one opiate antagonist with a bioavailability of less than 5% when administered orally represents a suitable substitute for the treatment of drug addiction. At the same time non-oral abuse is reliably prevented.

The present invention therefore relates to the use of a non-separable combination of morphine and at least one opiate antagonist with a bioavailability of less than 5% when administered orally for the preparation of a medicinal product to be administered only orally to treat drug addiction in humans, in particular for substitution therapy among drug addicts.

However, the present invention also relates to the use of a non-separable combination of an opiate, preferably morphine, and at least one opiate antagonist with a bioavailability of less than 5% when administered orally to prepare a medicinal product to be administered only orally to prevent non-oral opiate abuse among opiate addicts.

The substance combination according to the invention surprisingly represents an ideal substitute. In the course of studies it was shown that its receptor profile and its physiological degradation pathway are particularly advantageous within the framework of a substitution therapy.

Abuse:

The substance combinations according to the invention prevent their non-oral abuse.

By non-oral abuse is meant intravenous, pulmonary (through smoking), nasal, sublingual or rectal abuse. In these cases the drug addict attempts to achieve the intoxicating effect by application paths not provided for by the manufacturer of a corresponding preparation. For example a preparation is melted or dissolved and injected intravenously or a preparation is burnt on aluminium foil and the smoke inhaled (pulmonary abuse; foil smoking).

The selection according to the invention of antagonists having a low bioavailability when applied orally, i.e. a bioavailability of less than 5% when administered orally, and an agonist with a bioavailability that is adequate for physiological blood levels when administered orally, ensures that the combination preparation according to the invention leads to a good substitution result only if it is taken orally. If it is taken in other ways, for example by the intravenous, pulmonary, nasal or rectal route, where the first-pass metabolism through the liver and/or metabolism in the intestinal wall and the cleavage activity of the digestive enzymes are avoided, withdrawal symptoms occur directly, as the antagonist takes full effect.

Non-Separability:

Many drug addicts split up the combination preparations with which they are supplied within the framework of a substitution therapy, in order to gain access to the respective intoxicating ingredient. To this end, in the case of multilayered preparations they dissolve the individual layers in solvent, for example ethanol, and obtain the pure addictive drug by evaporating the thus-obtained solution. A manual separation also takes place, for example by scratching off or breaking open the outer envelope of a preparation and exposing the addictive drugs inside. The ingredients of preparations which consist of individual recognizable units, for example on the one hand tablets with the agonist and on the other hand tablets with the antagonist, can easily be separated from each other anyway.

As a result, a particular advantage of the present invention is that the patient, i.e. the drug addict, cannot separate the morphine or more generally the opiate from the antagonist.

Administration forms suitable for this purpose are for example those in which agonist and antagonist are present as a powder or granule mixture. Suitable powders can have grain sizes of 25 µm to 0.1 mm, suitable granules can have grain sizes of 0.1 mm to 2 mm (in each case the maximum size of all the particles present in the mixture). Determination of the particle sizes can be carried out by separation methods, wherein sieve separation is particularly suitable. With this embodiment, because of the mixing and visual indistinguishability of the different particles, it is not possible for the drug addict to separate with certainty the individual particles of the mixture into agonists and antagonists.

Administration forms in which agonist and antagonist are present embedded together in a matrix and for example compressed into a tablet are also suitable. Here too it is no longer possible for the drug addict to separate the active ingredients from the matrix. The result of dissolution in a solvent is that all the ingredients are equally dissolved and a separation with means available to the drug addict is no longer possible. Nor does a mechanical division of the matrix containing the active ingredients allow the agonist to be obtained separately from the antagonist.

In principle, in the present invention a non-separable administration form of agonists and antagonists is chosen which does not allow a separation of the mixture into agonists and antagonists by mechanical and/or visual separation methods, i.e. for example by visual inspection followed by manual separation of the different constituents of the mixture, or by dissolving the mixture and then evaporating and/or precipitating the individual constituents of the mixture.

An easy separability or solubility using physical or chemical methods, in particular simple household separation methods such as filtering through coffee filters, dissolution in easily accessible solvents, filtering through cigarette filters, straining, separation based on different molecular weight and/or different floating properties (skimming) is thus prevented.

Opiate:

In principle, within the framework of the use according to the invention for the prevention of non-oral abuse, all known opiates can be used in combination with a corresponding antagonist countering the effect of the opiate. These include for example morphine, codeine, papaverine and thebaine. Morphine is particularly preferred.

Morphine is used within the framework of the use according to the invention in the substitution therapy.

Morphine is an opiate with the formula:

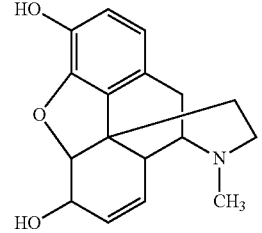 [SMILES: CN1CCC23c4c5ccc(O)c4OC2C(O)C=CC3C1C5]

Morphine, also colloquially called morphia, is a very effective painkiller which can be extracted from the seeds of the opium poppy. Just like heroin, it is addictive, but it is less effective.

According to the present invention morphine is administered in retarded or non-retarded form.

By a retarded form (or retard form) of a medicinal product is meant an administration form in which the release of the active ingredient is slowed down. Using retarded forms, the active ingredient can be released in the body in a controlled manner and thus prevent possibly dangerous concentration peaks of the active ingredient in the blood. Through the controlled release of the active ingredient, the medicinal product is effective for longer in the patient. The active ingredient therefore needs to be taken less often.

According to the present invention a retarded form of morphine is preferred. This can make it possible for the opiate to be taken only once or twice daily.

Within the meaning of the present invention the terms "retarded form", "retard form" and "sustained-release form" are used synonymously.

Through the use of morphine or more generally opiate in retarded form, the substitute needs to be taken less frequently. Because of the longer-lasting effect of the morphine, the drug addict's need to obtain a fresh supply of intoxicants as soon as possible is alleviated. In addition, the dangers of an overdose are alleviated by the retard form, as the active ingredient is passed into the blood in a controlled manner, avoiding concentration peaks.

Retarded forms of opiates and in particular of morphine are sufficiently known to a person skilled in the art. According to the present invention every retarded form of morphine and more generally opiate can be used. According to the present invention a formulation is preferred in which the morphine is adsorbed on a polymer, for example a hydrophilic polymer, and embedded in a matrix, for example a hydrophobic matrix. The antagonist is preferably also located in the matrix, in order to ensure the non-separability according to the invention. The polymer is preferably a cellulose polymer and the matrix a wax. On contact with the gastric juice the polymer forms a gel through which the active ingredient can pass only with a delay. Another preferred retard formulation is characterized in that, in a liquid administration form, the morphine is suspended in an ethyl cellulose polymer and released only with a delay. Another common retard form is a tablet coated with a protective layer. The protective layer dissolves only slowly in the gastric juice and the release of the active ingredient is correspondingly delayed.

The opiates, particularly the morphine, can be administered in all the usual administration forms according to the present invention. Physiologically acceptable salts such as hydrochlorides, hydrates, sulphates, chlorates and quaternary salts are preferred. Particularly preferred morphine salts are morphine hydrochloride, morphine sulphate pentahydrate, morphine chlorate, morphine methobromide and other quaternary morphine salts such as morphine-N-oxide.

The danger of the preparation according to the invention being improperly taken intravenously can also be further reduced by the opiate being present in retarded form.

The preparation according to the invention contains 1 to 2000 mg, preferably 100 mg to 1500 mg of opiate. The quantity can be adjusted according to the needs of the patient.

Antagonist:

According to the present invention the opiate is administered in combination with at least one antagonist. Naloxone or one of its derivatives or salts is a preferred opiate antagonist. Naloxone has the following structural formula:

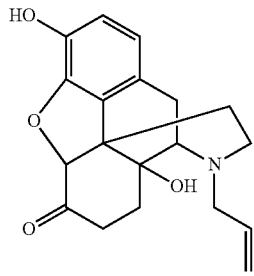 [SMILES: C=CCN1CCC23c4c5ccc(O)c4OC2C(=O)CCC3(O)C1C5]

The antagonist, in particular the naloxone, can be administered in all the usual administration forms according to the present invention. Physiologically acceptable water-soluble salts such as hydrochloride or hydrochloride dihydrate are preferred. The antagonist is present in the preparation according to the invention in either retarded or non-retarded form. The non-retarded form is preferred.

Naloxone acts as an opiate antagonist in completely the opposite way to opiate agonists such as morphine: naloxone blocks the opiate receptors and reduces the effect of the morphine. A correspondingly high dose of naloxone completely eliminates the effect of morphine, and there are withdrawal symptoms. This effect is known and is exploited for example to treat opiate poisoning by administering naloxone.

Remarkably, naloxone has a significant antagonistic effect when it is administered intravenously, but scarcely any when administered orally. The reason for this is that, when administered orally, naloxone experiences a pronounced first-pass metabolism and is therefore rapidly broken down. In other words the bioavailability of orally administered naloxone is very low, sometimes less than 5%, and the opioidal effect of the morphine is scarcely impaired by the naloxone. However, if taken intravenously or in some other improper way the naloxone would greatly impair the opioidal effect of the morphine. In other words, with the preparation according to the invention, the patient is forced to take the medicinal product orally. For drug addicts, the intravenous, nasal or pulmonary pathway is undoubtedly the administrative route of choice, because of the speed with which the effect ("kick") sets in. With the preparation according to the invention, the result of taking it intravenously would be merely frustration, however, as the effect of the morphine is greatly reduced by the intravenously effective naxolone, and in extreme cases even eliminated, which would lead to the immediate appearance of withdrawal symptoms.

The antagonists which can be used within the framework of the present invention have a bioavailability of less than 5%, preferably less than 3%, particularly preferably less than 1%. By bioavailability is meant in this case the percentage of the active ingredient which appears unchanged in the blood when the mixture according to the invention is administered orally. (The bioavailability of an intravenously injected medicinal product is by definition 100%. For a more detailed definition, reference is made to Rainer K. Liedtke, Wörterbuch der Klinischen Pharmakologie, Gustav Fischer Verlag, Stuttgart, N.Y., 1980. Bioavailability is also defined in WHO Annex 9, 1996.) The low bioavailability ensures that a drug addict does not feel a "kick" when he takes the preparation according to the invention, but a relatively low level of antagonists is maintained in the patient's blood. It is surprising in this connection that, despite the low bioavailability, a substitution therapy with the advantages listed below is made possible.

According to the invention, at least one antagonist is used. The use of one, two or three antagonists in combination with a corresponding opiate, preferably morphine, is preferred. The combination of morphine and naloxone is particularly preferred.

The possible combinations of retarded and non-retarded active ingredients comprise retarded morphine and non-retarded antagonists, retarded morphine and retarded antagonists, non-retarded morphine and non-retarded antagonists as well as non-retarded morphine and retarded antagonists. Naloxone can be the preferred antagonist in each case.

According to the invention the quantity of antagonists in the preparation is high enough to reduce the undesired side-effects caused by the morphine, for example constipation.

It was also shown that, due to the presence of naloxone, the patient's tolerance to morphine which would otherwise occur is reduced.

Thus the preparation according to the invention has the following surprising profile:
  reduction or avoidance of the constipation caused by morphine;
  reduction or avoidance of the development of morphine tolerance;
  prevention of an improper intravenous, inhalational or nasal intake (abuse);
  excellent suitability as a substitute;
  reduction or avoidance of the foul smell given off by substituted patients, due to the constipation caused by morphine;

reduction or avoidance of the sexual dysfunction triggered by substitutes.

Moreover, the use according to the invention can contribute to a reduction or avoidance of the change in the body mass index (BMI) as well as a reduction or avoidance of the tooth decay which is to be observed in patients prescribed a substitute.

According to the invention, 0.1 to 10 mg of naloxone, preferably 1 to 5 mg of naloxone are contained per tablet per 100 mg of retarded morphine.

A particularly preferred embodiment of the present invention is a preparation with 100 mg to 1500 mg of retarded morphine in combination with 1 mg to 5 mg of naloxone.

Although naloxone is preferably used as an additional active ingredient according to the present invention, in principle all opiate antagonists with a corresponding low bioavailability can be used when administered orally. Such compounds are known to a person skilled in the art. As regards quantity details and method of administration, what was said above concerning naloxone applies analogously to this substance.

The preparation according to the invention is characterized in that it cannot be taken intravenously, for the above reasons. The preparation according to the invention can be taken orally (e.g. as a solution or tablet). The corresponding administration forms are known to a person skilled in the art. Depending on the specific administration form, the preparation according to the invention contains the additives customary for this, which are also sufficiently known to a person skilled in the art and require no further explanation here.

The invention is explained in more detail by the following examples without being limited by them.

EXAMPLES

The morphine used in the following examples is a powder with a grain size <400 μm; manufacturer: McFarland. The naloxone used is supplied by Sanofi-Aventis and the Eudragit by Röhm GmbH, Darmstadt, Germany.

Example 1: Morphine/Naloxone Retard Capsules

The preparation of naloxone retard pellets and morphine retard pellets which are packed into a hard-gelatine capsule is described below:

Example 1A: Naloxone-HCl Retard Pellets

Formulation:

| Ingredient | Quantity/unit (mg) | Quantity/batch (g) |
|---|---|---|
| Naloxone HCl | 2.0 | 33.3 |
| Eudragit RSPO | 70.0 | 1166.7 |
| Eudragit RLPO | 8.0 | 133.3 |
| Stearic acid | 40.0 | 666.7 |
| Total | 120.0 | 2000.0 |

Method:

Naloxone HCl, Eudragit RSPO, Eudragit RLPO and stearic acid are mixed in a twin-cylinder mixer. The mixed material is continuously introduced into a twin-screw extruder and the resulting strands collected on a conveyor belt. The strands are cooled on the conveyor belt. The cooled strands are cut into pellets in a pelletizer. The pellets are screened and the desired screened portion collected.

Example 1B: Morphine-HCl Retard Pellets

Formulation:

| Ingredient | Quantity/Unit (mg) | Quantity/batch (kg) |
|---|---|---|
| Morphine HCl | 12.0 | 3.2 |
| Eudragit RSPO | 76.5 | 20.4 |
| Ethyl cellulose | 4.5 | 1.2 |
| Stearyl alcohol | 27.0 | 7.2 |
| Total | 120.0 | 32.0 |

Method:

Stearyl alcohol flakes are passed through an impact grinding mill. Morphine HCl, Eudragit RSPO, ethyl cellulose and stearyl alcohol are mixed in a twin-cylinder mixer. The mixed material is continuously introduced into a twin-screw extruder and the resulting strands collected on a conveyor belt. The strands are cooled on the conveyor belt. The cooled strands are cut into pellets in a pelletizer. The pellets are screened and the desired screened portion collected.

The pellets prepared in Examples 1A and 1B are packed into a hard-gelatine capsule in the ratio 1:1 and the latter is sealed.

Example 2: Opiate Agonist/Antagonist Retard Granules (Compressed into Tablets)

The preparation of retard tablets which contain morphine HCl and naloxone HCl is described below, wherein both active ingredients are present as granules. The granules containing the morphine and the naloxone are dispersed in a matrix with controlled release. The granules are combined with molten wax (stearyl alcohol) in order to obtain waxed granules which are then ground, mixed with other excipients and compressed into tablets.

Formulation:

| Ingredient | Quantity/unit (mg) | Quantity/batch (g) |
|---|---|---|
| Morphine HCl | 10.0 | 11.00 |
| Naloxone HCl | 0.50 | 0.55 |
| Spray-dried lactose | 68.75 | 75.62 |
| Povidone | 5.00 | 5.50 |
| Eudragit RS 30D (dry weight) | 10.00 | 11.00 |
| Triacetin | 2.00 | 2.20 |
| Stearyl alcohol | 25.00 | 27.50 |
| Magnesium stearate | 1.25 | 1.38 |
| Opadry white | 5.00 | 5.50 |
| Purified water | | 31.16* |
| Total | 127.5 | 140.25 |

*Remains only as residual moisture in the product

Method:

Grinding: Eudragit is softened with triacetin by mixing and naloxone HCl is dissolved in this solution.

Granulation: Morphine HCl, spray-dried lactose and povidone are introduced into a fluidized-bed granulator and the solution prepared in the preceding step is added.

Grinding: The granules are passed through a rotating fan mill.

Drying: If the moisture content of the granules is too high, they are dried.

Waxing: The granules are waxed by addition of molten stearyl alcohol during the mixing.

Cooling: The waxed granules are cooled in a fluidized-bed drier.

Grinding: The cooled and waxed granules are passed through a rotating fan mill.

Mixing: The ground and waxed granules are mixed with magnesium stearate.

Pressing: The resultant granules are compressed using a tablet press.

Coating: The opadry white is dispersed in purified water in order to obtain a coating solution which is applied to the tablet core.

Example 3: Hard-Gelatine Capsule Tablets with Opiate-Agonist/Antagonist Extrudates Formulation:

| Ingredient | Quantity/unit (mg) | Quantity/batch (g) |
| --- | --- | --- |
| Morphine HCl | 12.0 | 120.00 |
| Eudragit NE 30 D | 76.0 | 760.0 |
| Ethyl cellulose | 4.5 | 45.0 |
| Stearyl alcohol | 27.0 | 270.0 |
| Naloxone HCl | 0.5 | 5.0 |
| Hard-gelatine capsule | ✓ | ✓ |
| Total | 120.0 | 1200.0 |

The invention claimed is:

1. A method of treating an opiate-dependent or heroin-dependent individual in need of substitution therapy, the method comprising orally administering to the individual in need of such therapy an effective amount of an oral dosage form, the oral dosage form comprising a non-separable combination of morphine sulfate pentahydrate, and naloxone hydrochloride dihydrate, wherein the naloxone hydrochloride dihydrate is present at 1 mg per 100 mg of morphine sulfate pentahydrate, wherein the oral dosage form contains 2 mg of naloxone hydrochloride dihydrate, and wherein the morphine sulfate pentahydrate is formulated for sustained release.

2. The method of claim 1, wherein the oral dosage form reduces or prevents opiate-specific side effects.

3. The method of claim 1, wherein the naloxone hydrochloride dihydrate is formulated for sustained release.

4. The method of claim 1, wherein the morphine sulfate pentahydrate is: adsorbed on a polymer and embedded in a matrix; or suspended in an ethyl cellulose polymer.

5. The method of claim 1, wherein the oral dosage form is administered once or twice daily.

6. The method of claim 5, wherein the oral dosage form is administered once daily.

* * * * *